United States Patent [19]

Knowles et al.

[11] 3,937,696
[45] Feb. 10, 1976

[54] PROCESS FOR PREPARING HIGHER PURITY AZO COMPOUNDS

[75] Inventors: Richard N. Knowles; Earl P. Moore, Jr., Hockessin, both of Del.

[73] Assignee: E. I. Du Pont de Nemours & Co., Wilmington, Del.

[22] Filed: Apr. 2, 1974

[21] Appl. No.: 457,386

[52] U.S. Cl............. 260/192; 260/208; 260/92.8 W
[51] Int. Cl.$^2$........................................ C07C 107/02
[58] Field of Search..................................... 260/192

[56] References Cited
UNITED STATES PATENTS 3,170,913   2/1965   De Benneville et al. ........... 260/192
3,207,714   9/1965   De Benneville et al. ....... 260/192 X
3,783,148   1/1974   Fuchs................................. 260/192

Primary Examiner—Floyd D. Higel

[57] ABSTRACT

After an azonitrile is prepared by coupling an aminonitrile in the presence of a hypochlorite, the reaction mixture is acidified to a pH of 4 or less and an alkali metal, alkaline earth metal or quaternary ammonium nitrite, sulfite, bisulfite or thiosulfate, sulfur dioxide, nitrogen oxide, oxalic acid, formaldehyde or hydroxylamine is added as a reducing agent.

9 Claims, No Drawings

PROCESS FOR PREPARING HIGHER PURITY AZO COMPOUNDS

BACKGROUND OF THE INVENTION

Azonitrile compounds are particularly useful as catalysts in certain polymerization processes such as, for example, the emulsion, dispersion solution and bulk polymerization of vinyl chloride. However, the azonitrile compounds which are thus employed must have a certain minimum purity. U.S. Pat. No. 3,783,148 issued to Julius Fuchs on Jan. 1, 1974 describes a process for preparing azonitriles by coupling aminonitriles in the presence of a hypochlorite. While such a production method yields azonitriles which are eminently suitable for most uses, the azonitriles thus prepared are not sufficiently pure for use in some polyvinyl chloride polymerization processes.

SUMMARY OF THE INVENTION

It has now been found that higher purity azonitriles can be obtained when the reaction mixture obtained after the completion of a coupling reaction of aminonitrile compounds in the presence of a hypochlorite is acidified to a maximum pH of 4 and an alkali metal, alkaline earth metal or quaternary ammonium nitrite, sulfite, bisulfite or thiosulfate, sulfur dioxide, nitrogen oxide, oxalic acid, formaldehyde or hydroxylamine is added as a chemical reducing agent. This purification step is particularly useful in the production of 2,2'-azo-bis (2,4-dimethylvaleronitrile). The azonitrile which is obtained has a purity of 97 weight percent or higher.

DETAILED DESCRIPTION OF THE INVENTION

In the production of azonitriles by coupling aminonitriles in the presence of a hypochlorite as described in the Fuchs patent cited above, two molecules of an aminonitrile such as, for example, those described in U.S. Pat. No. 3,541,132 issued to Richard N. Knowles on Nov. 17, 1970, are coupled in the presence of a hypochlorite at a temperature above the freezing point of the reaction mixture and below 50°C. in a reaction solvent that contains at least 95% by volume of methyl or ethyl alcohol at the beginning of the reaction and at least 70% by volume of the methyl or ethyl alcohol at the end of the reaction. When the reaction is completed, water is added to precipitate the azo compound, and dissolve the chloride in the reaction mixture. Generally, from about 0.4 to 0.7 parts of water per part of reaction mixture are used although any amount of water may be used as long as the reaction mixture remains a slurry. The azonitrile can then be isolated by filtration. Either before or after the water is added but before the azonitrile is isolated, the pH of the reaction mixture is adjusted to a maximum of 4, generally from 3 to 1 and preferably 2 to 1.

Any acid or compound which will yield an acid in water may be used in the acidification step. For example, hydrochloric, sulfuric, phosphoric and the like acids may be used as well as sulfur dioxide, nitrogen dioxide and so on. Hydrochloric acid is preferred since the system already contains a high concentration of chloride ions. Any desired concentration of the acid or acid yielding material may be used.

After the pH adjustment is complete a chemical reducing agent is then added. Generally, sulfur dioxide, nitrogen oxide, salts that dissociate in an aqueous medium to yield nitrite, sulfite, bisulfite, thiosulfate and the like anions, including sodium, potassium, lithium, quaternary amino, magnesium, calcium and the like salts of any of the above anions may be used. Organic compounds such as oxalic acid, formaldehyde, and hydroxylamine and the like may also be used although the inorganic chemical reducing agents are preferred. Mixtures of any of the reducing agents may also be used. Sulfur dioxide is a preferred reducing agent particularly where it is also used as the acidifying agent.

The amount of the chemical reducing agent is determined by titrating a sample of reaction mixture which has been added to an acidified potassium iodide solution with a solution of sodium thiosulfate, preferably 0.1 normal. The iodide reacts with the oxidants in the reaction mixture and becomes iodine. The thiosulfate reduces the iodine thus formed back to the iodide. The amount of reducing agent used is based upon equivalents or moles of oxidizing impurity present in the reaction mixture. Any amount of reducing agent from 1.0 to 2.0 or more equivalents per equivalent of oxidant present can be used although 1.0 to 1.25 equivalents of reducing agent per equivalent of oxidant is preferred.

While the theory of the operation of the reducing agent at the prescribed pH in this invention is not entirely understood, it is hypothesized that intermediates which form during the coupling of the aminonitrile compound are hydrophobic and act as emulsion stabilizers. As a consequence, azonitrile emulsions which contain these intermediates do not break readily in a solvent such as methyl isobutyl ketone. Azonitrile emulsions which break slowly in such a test cannot be used in certain dispersion and emulsion polymerization processes for the production of polyvinyl chlorides, for example. The acidification and addition of the reducing agents of this invention, when carried out at the end of the synthesis of azonitrile compounds obviates this undesirable property and increases the purity of the azonitrile to greater than 97% by weight.

This result was particularly surprising since the acidification of the system would be expected to cause the precipitation of undesirable side reaction products which would severely contaminate the azonitrile product. For example, in the production of 2,2'-azobis(2,4-dimethylvaleronitrile), the acidification of the system would be expected to decompose the isobutyric salts in the reaction mixture to form isobutyric acid. The isobutyric acid would become absorbed into and trapped by the azonitrile product making removal by conventional washing techniques difficult at best. Since isobutyric acid is malodorous, a combined purity-pollution problem would result. Unexpectedly, no such problems arise when the improvement of this invention is employed. The azonitrile product which can be used without further purification has been found to be drier, non-oily, white in color and free-flowing. It is therefore easily processed into whatever form may be desired for its use. It has also been found that, while the improvement of this invention is operable when used as the last step in the production of azonitriles, particularly 2,2'-azobis(2,4-dimethylvaleronitrile), similar consistently excellent results are not obtained when an already isolated azonitrile is reslurried and subjected to this treatment.

The invention is further illustrated but is not intended to be limited by the following examples in which all parts and percentages are by weight unless otherwise specified.

EXAMPLE 1

60 grams of 2-amino-2,4-dimethylpentanonitrile of 88.2% purity are added simultaneously with 399 grams of 14.1% sodium hypochlorite solution to 860 ml. rapidly stirred methanol cooled at −5°C. so that addition is completed in 1 hour. The reaction mixture is then allowed to warm to 10°C. and held at that temperature for 10 minutes; 575 ml. of cold water are then added.

Titration of a sample of the mixture with 0.1 normal sodium thiosulfate solution for freed iodine following addition to acidified potassium iodide solution showed 0.038 equivalent oxidizing material present.

The cold reaction mixture was acidified to a pH of 2.0 with concentrated hydrochloric acid and 4.0 grams of sodium bisulfite (0.076 equivalent or 100% excess) dissolved in 10 ml. of water were added.

After 10 minutes the solid 2,2′-azobis(2,4-dimethylvaleronitrile) product was filtered, washed with water and dried. A test of the product with acidified potassium iodide showed no oxidizing impurity present (no iodine liberated).

An assay of the non-oily, white, free-flowing product showed a purity of 99%.

EXAMPLE 2

To a solution of 63.2 parts of 2-amino-2,4-dimethylpentanonitrile in 592 parts of methanol are added over a 20 minute period at −10°C. with agitation 377 parts of a 15% aqueous sodium hypochlorite solution. The reaction was then allowed to warm to 10°C. and held for 10 minutes. At this point methanol constitutes 74 volume percent of the aqueous solvent. The resulting reaction product was diluted with 500 parts of water and titrated with standard sodium thiosulfate as described in Example 1. About 0.015 equivalent of oxidizing agent was present. The resulting slurry was then acidified to a pH of 1.0 with 15% hydrochloric acid and 0.52 gram of sodium nitrite (0.015 equivalent) were stirred into the mixture. The precipitated 2,2′-azobis (2,4-dimethylvaleronitrile) was isolated by filtration and found to be non-oily, white and dry with a purity of 98%.

EXAMPLE 3

To a mixture of 276 parts of methanol and 129 parts of 10% aqueous calcium hypochlorite at −10°C. are added with agitation 15.6 parts of 2-amino-4-methoxy-2,4-dimethylpentanonitrile. The mixture was stirred for approximately 45 minutes while the temperature was allowed to rise to 10°C. At this point in the reaction methanol constitutes 75 volume percent of the aqueous solvent. Titration with sodium thiosulfate as described in Example 1 showed 0.045 equivalent of oxidizing agents in the reaction mixture. The reaction mixture was then acidified to a pH of 3 with 10% hydrochloric acid and 2.16 grams (.0675 equivalent) of $SO_2$ gas were added to the mixture, followed by 232 parts of water. The precipitated 2,2′-azobis (2,4-dimethylvaleronitrile), isolated by filtration, was found to be white and free-flowing and had a purity of 97.7%.

It is to be understood that any of the components and conditions mentioned as suitable herein can be substituted for its counterpart in the foregoing examples and that although the invention has been described in considerable detail in the foregoing, such detail is solely for the purpose of illustration. Variations can be made in the invention by those skilled in the art without departing from the spirit and scope of the invention except as set forth in the claims.

What is claimed is:

1. In a process for producing an azonitrile by coupling an aminonitrile in the presence of a hypochlorite, the improvement which comprises acidifying the reaction mixture to a pH of a maximum of 4 and adding an alkali metal nitrite, alkali metal sulfite, alkali metal bisulfite, alkali metal thiosulfate, alkaline earth metal nitrite, alkaline earth metal sulfite, alkaline earth metal bisulfite, alkaline earth metal thiosulfate, quaternary ammonium nitrite, quaternary ammonium sulfite, quaternary ammonium bisulfite, quaternary ammonium thiosulfate, sulfur dioxide, nitrogen oxide, oxalic acid, formaldehyde or hydroxylamine as a reducing agent after the coupling reaction is completed.

2. The improvement of claim 1 wherein the reaction mixture is acidified to a pH of from 3 to 1.

3. The improvement of claim 1 wherein the reaction mixture is acidified with hydrochloric acid.

4. The improvement of claim 1 wherein from 1.0 to 2.0 equivalents of the reducing agent is added per equivalent of oxidizing material contained in the reaction mixture.

5. The improvement of claim 1 wherein the reaction mixture is acidified with sulfur dioxide and the reducing agent is sulfur dioxide.

6. The improvement of claim 1 wherein the reducing agent is the sodium, potassium, lithium, quaternary ammonium, magnesium or calcium salt of a nitrite, sulfite, bisulfite or thiosulfate anion, sulfur dioxide or nitrogen oxide.

7. The improvement of claim 1 wherein the azonitrile is 2,2′-azobis (2,4-dimethylvaleronitrile).

8. The improvement of claim 1 wherein the azonitrile is produced at a temperature of above the freezing point of the azonitrile reaction mixture and below 50°C. in a solvent that contains at least 95% by volume of methyl or ethyl alcohol at the beginning of the reactor and at least 70% by volume of the methyl or ethyl alcohol at the end of the reaction.

9. The improvement of claim 1 wherein the reaction mixture is acidified to a pH of from 2 to 1.

* * * * *